United States Patent [19]

Johnson

[11] Patent Number: 5,766,240
[45] Date of Patent: Jun. 16, 1998

[54] ROTATABLE SUTURING RING FOR PROSTHETIC HEART VALVE

[75] Inventor: Keith M. Johnson, Coon Rapids, Minn.

[73] Assignee: Medtronic, Inc., Minneapolis, Minn.

[21] Appl. No.: 739,093

[22] Filed: Oct. 28, 1996

[51] Int. Cl.$^6$ ........................................................ A61F 2/24
[52] U.S. Cl. ............................................... 623/2; 623/900
[58] Field of Search ........................................ 623/2, 900

[56] References Cited

U.S. PATENT DOCUMENTS

| | | |
|---|---|---|
| Re. 30,507 | 2/1981 | Kaster . |
| 3,099,016 | 7/1963 | Edwards . |
| 3,396,409 | 8/1968 | Melrose . |
| 3,723,996 | 4/1973 | Raible et al. . |
| 3,727,240 | 4/1973 | Child . |
| 3,763,548 | 10/1973 | Anderson . |
| 3,781,969 | 1/1974 | Anderson . |
| 3,800,403 | 4/1974 | Anderson et al. . |
| 3,835,475 | 9/1974 | Child . |
| 3,903,548 | 9/1975 | Nakib ........................... 623/2 |
| 3,997,923 | 12/1976 | Possis . |
| 4,197,593 | 4/1980 | Kaster et al. . |
| 4,225,980 | 10/1980 | Ramos Martinez .......... 623/2 |
| 4,364,126 | 12/1982 | Rosen et al. ................. 623/2 |
| 4,535,483 | 8/1985 | Klawitter et al. ............ 623/2 |
| 4,612,011 | 9/1986 | Kautzky ........................ 623/2 |
| 4,680,031 | 7/1987 | Alonso . |
| 4,743,253 | 5/1988 | Magladry ..................... 623/2 |
| 4,790,843 | 12/1988 | Carpentier et al. .......... 623/2 |
| 4,935,030 | 6/1990 | Alonso . |
| 5,032,128 | 7/1991 | Alonso . |
| 5,071,431 | 12/1991 | Sauter et al. ................. 623/2 |
| 5,178,633 | 1/1993 | Peters . |
| 5,397,346 | 3/1995 | Walker et al. . |
| 5,487,760 | 1/1996 | Villafana . |

FOREIGN PATENT DOCUMENTS

| | | | |
|---|---|---|---|
| 2241304 | 8/1991 | United Kingdom ........... 623/2 |

*Primary Examiner*—Michael J. Milano
*Assistant Examiner*—Tram Anh T. Nguyen
*Attorney, Agent, or Firm*—Reed A. Duthler; Harold R. Patton

[57] ABSTRACT

An implantable prosthetic heart valve with a suturing ring having an interiorly disposed split ring of constant diameter for securing the suturing ring fabric to the heart valve body and providing a constant rotational torque for facilitating rotation of the heart valve body with respect to the suturing ring. The split ring is formed of a stiff band having opposed split ring ends that are drawn together and held in place by fixation cords. The split ring may include flanges extending in the inflow and/or outflow directions to inhibit passage of suture needles through inflow and/or outflow rim bands of the suturing ring fabric to encourage proper surgical installation. The flanges may be extended in the inflow and/or outflow directions sufficiently to increase blood flow velocity past the inflow and/or outflow rim bands and discourage pannus growth over the interface of the respective rim bands and valve body flanges and into the valve body annulus and to provide added safety by forming a barrier against impingement of the occluder by suture tails and heart tissue.

33 Claims, 5 Drawing Sheets

ROTATABLE SUTURING RING FOR PROSTHETIC HEART VALVE

CROSS-REFERENCE TO RELATED APPLICATION

Reference is hereby made to commonly assigned, co-pending U.S. patent application Ser. No. 08/547,854 filed Oct. 25, 1995 for HEART VALVE SUTURING RING WITH SURFACE COATING TO INHIBIT TISSUE INGROWTH in the name of Mark C. Shu et al.

FIELD OF THE INVENTION

The present invention generally relates to an implantable prosthetic heart valve having a fabric suturing ring within which the valve body may be rotated by applied rotation torque to an optimum orientation after the suturing ring is surgically implanted, and particularly to an improvement in a simplified suturing ring attachment to the heart valve body providing relatively consistent rotation torque and inhibiting intrusion of suture tails and tissue ingrowth into the valve mechanism.

BACKGROUND OF THE INVENTION

Modern implantable prosthetic mechanical heart valves are typically formed of an annular valve seat in a relatively rigid valve body and one or more occluding spheres, disks or leaflets that are movable between a closed, seated position in the annular valve seat and an open position in a prescribed range of motion. Such mechanical heart valves may be formed of blood compatible, non-thrombogenic materials, typically currently comprising pyrolytic carbon and titanium, with hinge mechanisms and/or pivoting guides prescribing the range of motion of the disk or leaflets. By way of comparison, some prosthetic tissue valves are formed from treated integral swine valve leaflets and valve annulus structure mounted to an annular valve body.

Modern prosthetic heart valves are often provided with a suturing ring surrounding the valve body that is sewed by the surgeon to the peripheral tissue of a natural heart valve orifice (the "valvar rim") after surgical removal of damaged or diseased natural valve structure. Many methods of attaching rotatable and non-rotatable suturing rings to annular valve bodies are disclosed in the prior art. Early prosthetic mechanical heart valves of the type shown in U.S. Pat. No. 3,099,016, for example, employed a spherical occluder trapped in a cage and movable between an open position at the end of the cage and a seated position against a circular valve seat in a circular valve body connecting the cage struts in response to blood flow. The cage and valve body were formed of flexible plastic, and a fabric suturing ring is formed about the valve body. In order to stabilize the plastic valve body and ensure that the valve seat remains circular over time, the fabric suturing ring was tightly bound in an interference fit against an outer annular groove in the valve body by a three piece, stainless steel, interrupted clamp ring held in place by a binding wire. The suturing ring was formed about the assembled clamp ring, and the resulting suturing ring was not rotatable with respect to the valve body. Because of the symmetric nature of the cage and spherical occluder, there was no need to rotate or advantage in rotating the valve cage to the heart structure after suturing the suturing ring in place.

In a further early mechanical heart valve design of the type shown in U.S. Pat. No. 3,396,409, a fabric suturing ring is formed in multiple fabric layer wraps about a stainless steel or PTFE ring of circular cross-section. The suturing ring is fitted into a pronounced outer annular groove surrounding the valve body and it is not suggested that it may be rotated. No explanation is provided as to how the suturing ring is formed or placed in the groove. It appears from the figures that a considerable compression of the fabric wraps against the deep cut sides of the groove result in an interference fit that would inhibit rotation even if it were suggested.

The suturing ring and valve body of more recent prosthetic heart valves having assymmetric valve mechanisms are frequently fabricated so that they may be rotated with respect to one another by the application of rotation torque. By rotating the valve body within the suturing ring, the surgeon can adjust the angular orientation of the valve mechanism in the path of blood flow so that proper operation without interference from the surrounding heart structure can be obtained or so that blood flow past the open valve mechanism can be diverted into a preferred direction. Such adjustment of the orientation by rotation of the valve body requires a rotational torque sufficiently small as to avoid damage to the sutured valvar rim or loosening of the sutures, and yet sufficiently great so that the valve body, when properly positioned, does not further rotate during chronic implantation.

Figure 1:
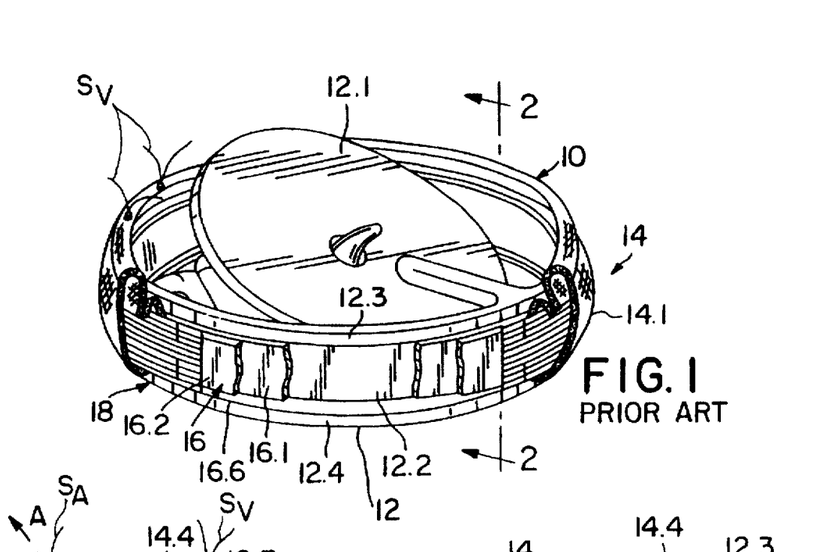
FIG. 1 is a perspective view in partial exposed section of a prior art prosthetic heart valve.
Figure 2:
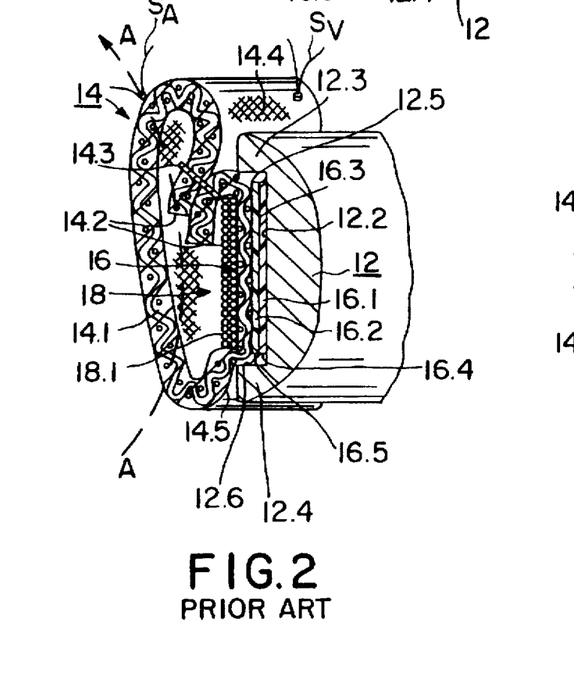
FIG. 2 is a cross-section view of the prior art prosthetic heart valve of FIG. 1.

Typical rotatable suturing rings for asymmetric mechanical valves are shown in U.S. Pat. Nos. 3,727,240, 3,763,548, 3,781,969, 3,800,403, 3,835,475, 4,197,593 and Re. 30,507. FIGS. 1 and 2 are reproduced from the above-referenced '593 patent and also are fair representations of the construction of the heart valve and suturing ring of the Medtronic® Hall® valve intended for aortic implantation sites. The mechanical heart valve 10 has an annular valve body 12 supporting an operating valve structure of pivots and guides that interact with a pivoting disc 12.1 to guide it between seated and open positions. The annular valve body 12 is desirably rigid, and may be made of titanium or reinforced pyrolytic carbon or the like. As depicted in the drawing, the valve body has an exterior annular wall 12.2, the surface of which is desirably generally flat and an interior wall defining the valve annulus and seat for the occluder disk when in the closed position. Flanges 12.3 and 12.4 extend generally radially outwardly from the exterior wall 12.2 at or adjacent to the upper, or outflow, and lower, or inflow, rims of the valve body 12. The flanges 12.3 and 12.4 therefore have diameters exceeding the diameter of the band-shaped exterior wall 12.2. The opposed, generally parallel surfaces 12.5, 12.6 of the flanges 12.3, 12.4 are thus spaced apart a predetermined distance in the direction of flow, and these surfaces, including the exterior wall 12.2, define an annular, desirably generally flat-bottomed, groove for receiving rotatable suturing ring 14.

In the fabrication depicted in FIGS. 1 and 2, the flat-bottomed groove around the exterior of the valve body is lined with a pair of slip rings 16 that are provided to reduce friction between the flat bottomed groove and the fabric suturing ring 14 after it is formed as described below. The slip rings 16 comprise two, generally flat rings with inner slip ring 16.1 bearing against the annular exterior wall 12.2 between the flange surfaces 12.5, 12.6, and outer slip ring 16.2 overlying inner slip ring 16.1. As suggested in the '593 patent, one or both of the slip rings 16.1, 16.2 may be formed of polytetrafluoroethylene (PTFE) or a stiff, rigid material, e.g., sapphire or pyrolytic carbon or a metal, e.g. stainless steel. In the '593 patent, the preferred embodiment employs slip rings 16.1, 16.2 each pre-formed of a narrow, flattened PTFE ribbon ring which can be manually positioned about the exterior wall 12.2 with the ends of each ring 16.1, 16.2 being closely adjacent one another or in actual abutting contact. The closely adjacent or abutting ends of the inner ring 16.1 are not aligned with the ends of the outer ring 16.2, so that the ends of the respective rings do not interfere with one another during rotation of the valve body 12 within the suturing ring 14. In practice it has been found that a single PTFE slip ring can also be substituted for the inner and outer slip rings 16.1, 16.2.

The suturing ring 14 comprises a fabric strip 14.1 made of synthetic fiber, such as polytetrafluoroethylene (e.g., "Teflon TFE") or polyester (e.g., "Dacron"), of a mesh weave having interstices permeable to tissue ingrowth. The fabric strip 14.1 has longitudinal edges 14.2 which are sewn together to form a seam 14.3, and first and second axial ends that are also sewn together. The strip 14.1 is thereby formed into a torus shaped or annular shaped suturing ring 14 having an interior directed minor surface adapted to be fitted against the outer slip ring 16.2 or single slip ring. The depicted flattened toroidal shape is particularly suitable for aortic valve replacement. Artificial heart valves intended for mitral valve replacement have pronounced radially extending flanges formed of a wider fabric strip 14.1 as shown, for example, in U.S. Pat. No. 4,930,030. However, the suturing ring 14 may have any desired cross-section profile.

The suturing ring 14 may also be filled with a biologically acceptable, spongy material, such as silicone rubber or polyurethane or hydrogel and the filled suturing ring may be formed and shaped as desired. Alternative shapes are shown, for example, in the above-referenced '548, '969 and '475 patents. In practice, the Medtronic® Hall® valve suturing ring 14 is not filled in either aortic or mitral valve configurations.

Before the suturing ring fabric 14.1 is sewn together at seam 14.3, it must be secured within the flat bottomed groove of the annular valve body and against the outer slip ring 16.2. To do so, a series of cord wraps 18.1 are wound overlying the fabric 14.1 and compressing it against outer ring 16.2 or the single slip ring. A single cord 18 may be employed to make all of the wraps, or several wraps may be made with each of several cord lengths.

The cord(s) 18 employed in the 593 patent and in the fabrication of the Medtronic® Hall® pivoting disk heart valve are of a heat-relaxable material such as braided polyester ("Dacron"). A particularly desirable cord is 2-0 "Tevdek II", which is a polytetrafluoroethylene ("Teflon TFE"-) impregnated, braided polyester ("Dacron") suture sold by the Deknatal Company.

Once the cord wraps 18.1 are wound against the inner surface of the suturing ring fabric 14.1, the cord ends are tied together. When the cord(s) 18 are tightened at ambient, room temperature, the suturing ring 14 is tightly bound against the slip rings 16, and a high rotation torque is necessary to achieve any rotation of the valve body 12 with respect to the suturing ring 14.

The suturing ring seam 14.3 and ends are then sewn together to form the flattened toroidal shape or sewn with a ring shaped flange. As described further in the '593 patent, the assembled suturing ring 14 and valve body 12 are then subjected to a low temperature heat treatment operation that results in elongation of the cord(s) 18 and loosening of the suturing ring 14 with respect to the slip rings 16 and valve body 12. This effects a loosening of the fit of the sewing ring 14 with respect to the annular exterior wall 12.2 and the slip ring(s) 16 to a degree that enables the valve body 12 to be rotated after implantation to a desired orientation through the application of a rotation torque to the valve body 12. Assembly of the heart valve 10 is then completed by insertion of the pivoting disk 12.1 into the valve body 12 in the manner described in the above-referenced '593 patent.

In the above-referenced '548, '969, '403 and '469 patents a further approach is described wherein heat shrink sleeves are used instead of the heat relaxed cord(s) 18. The heat shrink sleeves are formed in a continuous ring having an initial inner diameter allowing the sleeve to be fitted over the suturing ring fabric and then subjected to heat to shrink the inner diameter to fit within the annular outer surface of the valve body.

In both of these approaches, control of the degree to which the retaining cord or sleeve is either loosened or shrunk by the heat treatment process is difficult. In order to obtain satisfactory yields of acceptable heart valves, it is necessary to specify relatively wide tolerances for the rotational torque. Removal and installation of a new suturing ring is required if the tested suturing ring rotational torque falls outside the specified range. Such rework of some percentage of the heart valve assemblies adds to overall manufacturing expense. Rework of a significant percentage of tested valve assemblies may be required if the time and temperature of the heat treatment varies from the specified values.

Moreover, such prosthetic heart valves are supplied in a variety of sizes and types to hospitals in sterile containers and may not be used for many years. After a period of years, the cords and rings may tighten or loosen and the rotation torque can change. In addition, the valve may be re-sterilized prior to use, and the applied heat can affect the rotation torque. The causes are not fully understood, but the cumulative affects of time and temperature coupled with wide manufacturing tolerances and can make it difficult or too easy to rotate the suturing ring. Typically, the suturing ring rotational torque increases.

In certain other mechanical heart valves having a valve base that is typically formed of pyrolytic carbon as shown in U.S. Pat. Nos. 4,935,030, 5,035,709, 5,178,633, 5,397,346, 5397,348, and 5,487,760, for example, a continuous metal stiffening band is provided between the outer surface of the valve body and the suturing ring to strengthen the pyrolytic carbon valve base. In these designs, combinations of stiffening rings, multiple capture rings inside the suturing ring fabric, and mating grooves and lock wires, in certain cases, are combined with the toroidal fabric suturing ring to complete the assembly. The assemblies are complex and relatively expensive in parts and in manufacture.

As described in the above-referenced Shu et al. application, the fabric 14.1 of the typical suturing ring of the type shown in FIGS. 1 and 2 is porous and tear resistant so that needles and sutures pass through it when the suturing ring is sutured in place. Clinical studies indicate that a type of fibrous tissue forms on the suturing ring fabric 14.1 as a result of the initial deposition of thrombus and its subsequent organization into avascular, that is tissue without vascularization, fibrous tissue. Normally, this is not a clinical problem, particularly if care is taken to avoid stitching the suturing ring in place with sutures extending through the outflow rim band 14.4 and/or the inflow rim band 14.5, and the thin layer tissue formation and shallow growth into the fabric weave interstices is viewed as a positive factor in the stabilization of the suturing ring 14. Sometimes, however, a thick, fibrous tissue is evolved through granulation tissue and the growth of capillaries in it. This type of fibrous tissue not only extends into the interstices of suturing ring fabric 14.1 but also covers the suturing ring 14, and may produce procoagulant activity. More significantly, this type of fibrous tissue often becomes excessively thick as it continues to grow over the suturing ring 14 superior to the rim of flange 12.3 and inferior to the rim of flange 12.4, which may be encouraged when sutures are tied off in the outflow and/or inflow rim bands 14.4, 14.5. The intrusion of the tissue growth into the annular opening of valve body 12 can interfere with the range of motion of the leaflets or disk 12.1. This excessive growth is referred to in the literature as "pannus" overgrowth.

In the implantation of such heart valves, the surgeons are instructed to carefully direct curved suture needles through the valvar rim and the periphery of the suturing ring fabric 14.1 so that the sutures enter and exit the fabric 14.1 at a distance away from the interface with the valve body 12. Moreover, the suture needle should be passed through the fabric 14.1 in a manner to avoid penetrating and possibly severing the cord(s) 16 and the seam 14.3. Referring again to FIG. 2, surgeons are instructed to follow a curved suture path in the direction of arrow A—A to avoid penetrating these structures and so that the resulting acceptable suture knot and tails $S_A$ of the tied off suture are out of interference with valve structure. If these instructions are not carefully followed unacceptable suture knots and tails $S_U$ (examples shown in FIGS. 1 and 2) may be tied off so close to the interface that they may be flushed into the valve orifice and interfere with closure or opening of the valve mechanism. Many sutures extending around the suturing ring 14 are required to implant the valve, and the valve mechanism may be stuck partially open or closed by unacceptable suture knots and tails $S_U$, leading to severe complications.

Accordingly, it is desirable to provide a suturing ring attachment mechanism and process that results in fewer failures to rotate within a fairly narrow specification of rotational torque.

It is also desirable that a suturing ring for an artificial heart valve be provided that inhibits or minimizes tissue ingrowth into the valve body annular opening yet acts to stabilize the valve suturing ring.

It is further desired to provide such a suturing ring that discourages improper placement of attachment sutures during surgical implantation of the heart valve.

SUMMARY OF THE INVENTION

It is therefore an object of the present invention to provide a simplified suturing ring construction and fabrication process that provides for uniform rotational torque that is not dependent on close adherence to time and temperature in a heat treatment process.

It is a further object of the invention to simplify the fabrication process and number of components used in attaching the suturing ring to the valve body.

It is a still further object of the present invention to provide a suturing ring attachment mechanism that advantageously may be employed to shape the suturing ring in a manner that decreases pannus overgrowth.

It is yet a further object of the invention to provide embodiments of a heart valve suturing ring mechanism that inhibits placement of suture knots and tails too close to the valve annulus and thereby diminishes the chance that they will flow into and interfere with the valve mechanism.

A first aspect of the present invention is realized in an improved attachment method and apparatus for attaching the suturing ring around the annular exterior surface of a valve body wherein the annular exterior valve body surface is formed with a rotational guide, extending around the circumference of the valve body between inflow and outflow valve rims for cooperative retention of the suturing ring through frictional interaction with a section of the suturing ring fabric trapped between the rotational guide and a tracking surface of a split ring within the suturing ring fabric. The suturing ring is formed of a toroidal shape fabric tube and a stiff, split ring formed of a band extending between opposed split ends. An interior tracking surface is formed in the interior surface of the band in mating relationship with the rotational guide. The opposed split ends are maintained in contact, whereby a continuous gap is maintained between the split ring interior surface and the rotational guide of the valve body providing a consistent rotational torque that is required to rotate the valve body with respect to the suturing ring falling within narrow specifications and not subject to variation over time or affected by exposure to elevated temperatures during sterilization.

In a first preferred embodiment, the rotational guide of the exterior surface of the valve body is formed of a flat-bottomed groove of a width defined by opposed surfaces of upper, or outflow, and lower, or inflow, valve body flanges. The split ring is formed of a circular band of stiff material that is split at one location to form the opposed split ends allowing the band inner diameter to be increased slightly to fit over a valve body flange by drawing the split ends apart. The band has a substantially flat major interior surface and a major exterior surface having a groove formed therein for receiving a contact maintaining means e.g., a tightening cord, wire or further band, that is placed therein to draw and retain the opposed split ring ends together.

In one preferred variation, the split ring band has a width that fits within the flat-bottomed groove of the valve body with a continuous (but not necessarily constant) gap extending between each band edge and opposed surface of the adjacent valve body flange and between the flat major interior band surface and the opposed flat-bottomed groove surface. The band is self centering within the flat-bottomed groove and entraps the suturing ring fabric in a relatively uniform gap between the opposed surfaces of the band and the valve body exterior surface. The rotational torque is established by the friction of the compressed fabric in the gap and against the opposed tracking surfaces of the band and the flat-bottomed groove rotational guide. The minimum gap width and major contributor to the specified rotational torque may be defined between the opposed band edges and the opposed faces of the upper and lower flanges or between the opposed interior tracking surface of the band and the flat-bottomed groove.

In a further embodiment, the arrangement of the flat-bottomed groove and the flanges are reversed. The exterior surface of the valve body is formed with one or more raised circular flanges generally intermediate the inflow and outflow rims of the valve body providing the rotational guide. The split ring is formed with one or more grooved tracking surface in the interior wall thereof with greater dimensions than the raised circular flanges so that the raised circular flanges and the suturing ring fabric may be received in the continuous gap therebetween. Again, the opposed split ends are drawn and fixed together by suitable attachment means fitted within grooves extending around the band exterior surface.

In a further embodiment, the band is formed with one or two stepped band flanges that extend in the inflow and/or outflow directions over the inflow and outflow valve body flanges or otherwise to the inflow and outflow edges of the valve body. The suturing ring fabric tube extends over the band flanges. This extension generally prevents suturing needles from exiting the suturing ring fabric too close to the interface between the fabric and the edge of the valve body.

In a still further embodiment of the invention, the band flanges are extended still further in the inflow and/or outflow directions in order to increase the blood flow velocity at the junction of the suturing ring fabric with the valve body to discourage growth of pannus from the suturing ring fabric and into the valve body orifice. It is theorized that this modification will eliminate homeostasis or flow stagnation regions at the junction leading to reduction in pannus formation. Moreover, the extension prevents the suture knots and tails and any adjacent tissue, e.g., chordae, from extending over the extended band flanges into the valve body annulus and interfering with valve mechanism function.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The present invention may be practiced in a number of embodiments in improving conventional rotatable suturing rings for prosthetic mechanical and tissue heart valves. The following description illustrates the practice of the invention in preferred embodiments of a suturing ring mounted on a mechanical heart valve body of the type described in the above-referenced '593 patent, incorporated herein by reference, and commercially employed in the Medtronic® Hall® heart valve. It will be understood that the instant invention is not limited to any particular operating valve structure and indeed is applicable to pivoting disk valves, floating disc valves, valves with multiple flaps or closures, and the like. All of these valves, however, are characterized by having an annular valve body carrying a circumferential, rotatable suturing ring permitting the rotation of the valve after the suturing ring is sutured to the valvar rim remaining after removal of a patient's diseased heart valve.

Figure 3:
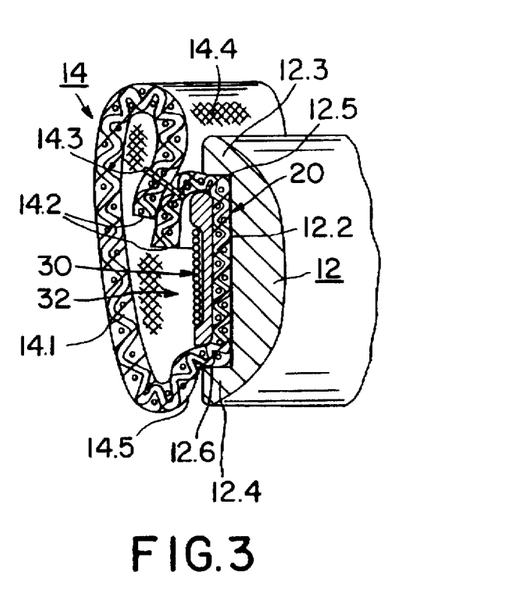
FIG. 3 is a cross-section view of a first embodiment of the present invention which may be implemented in mechanical heart valves of the type depicted in FIGS. 1 and 2.
Figure 4:
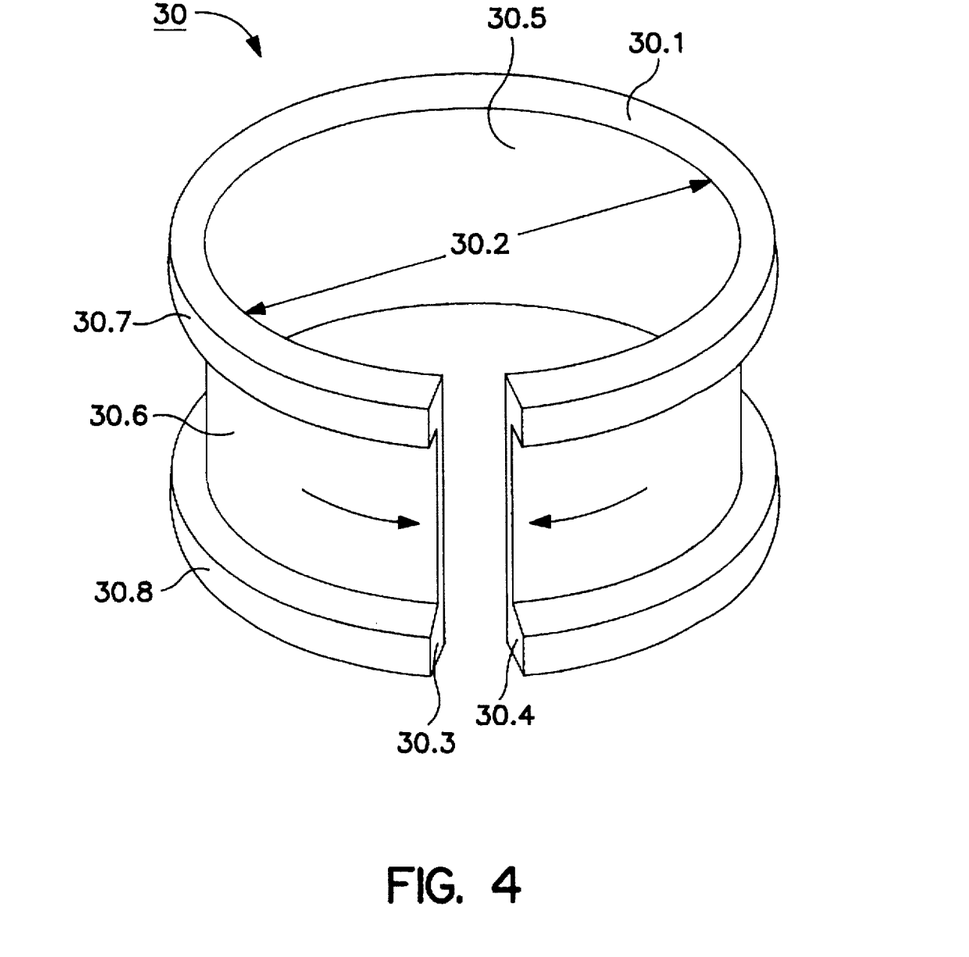
FIG. 4 is a perspective view of the split ring employed in the embodiment of FIG. 3

Turning to FIGS. 3 and 4, a first embodiment of the improved suturing ring and valve body of the invention is depicted employing a split ring 30 that is formed of a stiff circular band 30.1 of stainless steel or titanium, for example, having a fixed inner diameter 30.2 that is defined when the split ends 30.3 and 30.4 are brought together. The circular band 30.1 has a flat interior surface 30.5 shaped to conform to the flat-bottomed groove formed by the exterior wall 12.2 and a width that is less than the width of the exterior wall 12.2 between the upper and lower split ring flanges 12.3 and 12.4. An exterior single groove 30.6 (or multiple grooves) is formed in the exterior surface of circular band 30.1 having outflow and inflow side flanges 30.7 and 30.8. The groove 30.6 is provided for receiving at least one wrap of a binding means, e.g. a cord or wire 32 as shown in FIG. 3 and protecting it from suture needles used by the physician during implantation of the heart valve.

In the assembly depicted in FIG. 3, an annular section of the suturing ring fabric 14.1 is first fitted around the exterior surface of the valve body 12. The suturing ring fabric 14.1 is preferably woven into a circular fabric band of a single piece without any seams so that no seam is in the gap 20 when the fabric band is fitted around the valve body 12. The annular section of fabric 14.1 is laid into the flat-bottomed valve body groove formed by the exterior surface 12.2 and the adjacent valve body flanges 12.3 and 12.4.

Then, the split ends 30.3 and 30.4 of band 30.1 are drawn apart to expand diameter 30.2 and allow the interior tracking surface 30.5 to slip over the fabric 14.1 and one or the other of the valve body flanges 12.3 or 12.4. After the split ring band 30.1 is centered over the flat-bottomed valve body groove, it is compressed until the split ends 30.3, 30.4 abut one another, thereby providing the fixed inner diameter 30.2 and defining the gap 20.

To hold the split ends 30.3 and 30.4 in place, a cord 32 of suture material or wire or the like is wrapped around the outer surface within band groove 30.6 and tied. Alternatively, a continuous heat shrink band could be used that is slipped around the band groove heat and shrunk into place. Or a continuous NiTiNol band or ring could be used that can be expanded at a certain temperature to fit around the band groove 30.6 and then contracts tightly within the band groove when brought to body temperature. After the band 30 is secured, the suturing ring fabric 14 is sewn together at seam 14.3 to complete the fabrication of the depicted flattened toroidal shape suturing ring 14.

When the suturing ring 14 is completed, a continuous gap width is provided between the interior surface 30.5 and the outer valve body surface 12.2 within which an annular section of suturing fabric 14.1 is frictionally entrapped. The gap 20 extends continuously but not necessarily with a constant gap width between the upper and lower band edges and the opposed flange surfaces 12.5 and 12.6. The band 30 is self centering within the flat bottomed groove and entraps the suturing ring fabric 14.1 in the continuous gap 20. The rotational torque is established by the friction of the compressed annular section of fabric 14.1 in the gap 20 against these opposed surfaces of the band 30 and the valve body 12. The minimum gap width and major contributor to the specified rotational torque may be defined between the opposed band edges and the opposed upper and lower flange surfaces 12.5 and 12.6 or between the opposed band interior surface 30.5 and the valve body exterior surface 12.2.

For example, the gap 20 may be specified to be constant and on the order of 0.25 mm and the fabric may have an uncompressed thickness of 0.27 mm thereby compressing the annular section of suturing ring fabric 14.1 within gap 20. The resulting cushioning of the band 30.1 by the compressed fabric section self centers the suturing ring 14 within the flat-bottomed groove between the opposed flange surfaces 12.5 and 12.6.

In this manner, the compressed suturing ring fabric 14.1 tends to equalize the continuous gap 20 between the interior surface and edge surfaces of the split ring 30 and the opposed exterior surfaces 12.2, 12.5 and 12.6 of the valve body 12 all the way around the valve body 12. An annular section or band of the suturing ring fabric 14.1 is received in the gap 20 and frictionally engages these opposed surfaces of the split ring 30 and valve body 12. The frictional engagement over the opposed surfaces provides a consistent frictional force that may be overcome by rotational torque applied between the valve body 12 and the suturing ring 14 for rotation thereof. As a result, a consistent rotational torque required to rotate the suturing ring 14 with respect to the valve body 12 can be specified and readily attained in manufacturing. A minimum number of easily fabricated parts are employed and the heat treatment steps are eliminated, thereby reducing manufacturing expense and eliminating a substantial amount of rework.

Figure 5:
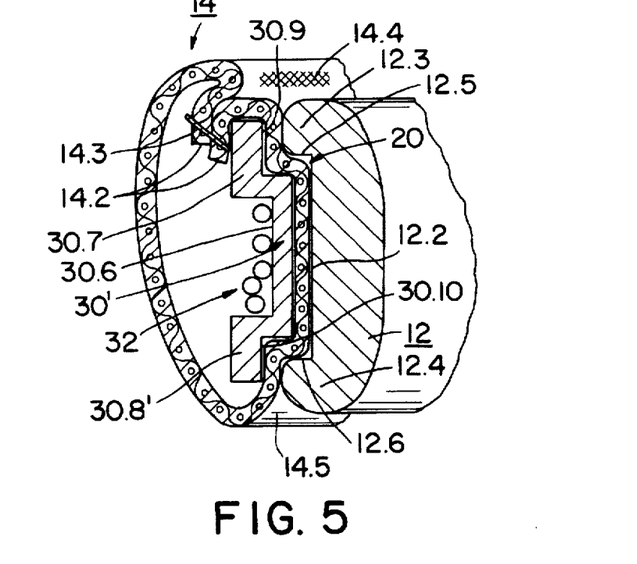
FIG. 5 is a cross-section view of a second embodiment of the present invention which may be implemented in mechanical heart valves of the type depicted in FIGS. 1 and 2.
Figure 6:
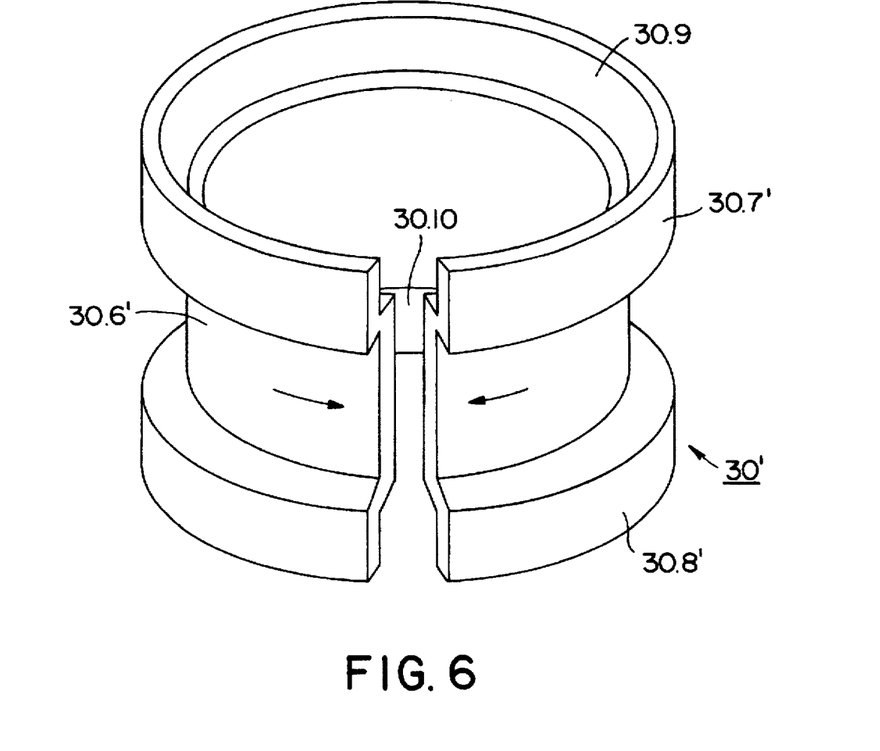
FIG. 6 is a perspective view of the split ring employed in the second embodiment of FIG. 3

Turning to FIGS. 5 and 6, a second embodiment of sewing ring 14 is depicted wherein an outflow band flange 30.7' and an inflow band flange 30.8' are extended outward and over the outer diameter surfaces of the corresponding upper and lower valve body flanges 12.3 and 12.4. The interior diameter 30.2 is increased in interior band shaped surfaces 30.9 and 30.10 to compensate for and provide clearance from the increased diameter of the valve body flanges 12.3, 12.4. The continuous gap 20 then extends between all interior surfaces of the split ring 30' and the corresponding valve body exterior opposed surfaces. The gap width may be specified to be constant throughout or may differ in differing areas, for ease of manufacturing, e.g. by widening the specified gap width between the extended band flanges 30.7', 30.8' and the outer diameter surfaces of the valve body flanges 12.3 and 12.4. Again, the suturing ring 30' self centers within the valve body flat-bottomed groove. This embodiment discourages suturing through the outflow and inflow rim bands 14.4 and 14.5. In a further modification, only the extended outflow or inflow band flanges 30.7' or 30.8' may be provided or their widths in the axial direction may differ from one another.

Figure 7:
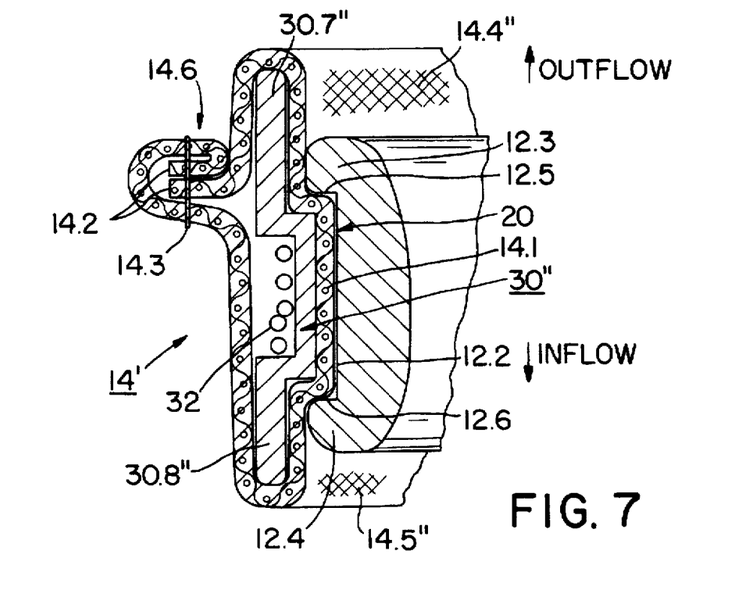
FIG. 7 is a cross-section view of a third embodiment of the present invention which may be implemented in mechanical heart valves of the type depicted in FIGS. 1 and 2.
Figure 8:
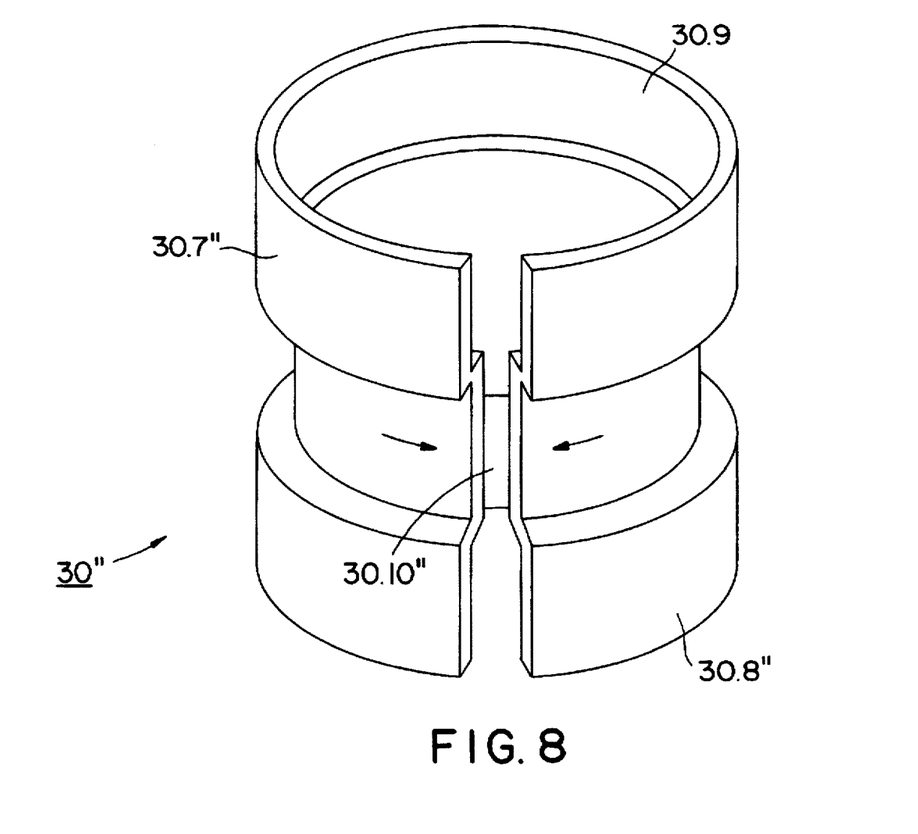
FIG. 8 is a perspective view of the split ring employed in the third embodiment of FIG. 7.

Turning to FIGS. 7 and 8, a third embodiment of the present invention is depicted wherein the sewing ring 14' is shown with a suturing flange 14.6, for example, and extends in the outflow and inflow directions so that the outflow and inflow rim bands 14.4 and 14.5 are in high blood flow regions and relatively far away from where the suture ends are knotted and severed forming suture tails. The suturing ring 14' is formed with a fabric flange 14.6 for suturing to the valvar ring in a manner well known in the art. This embodiment of the invention may also be practiced with a toroidal shape suturing ring 14 depicted in the other figures.

The extended outflow band flange 30.7" and inflow band flange 30.8" are extended outward and over the corresponding valve body outflow and inflow flanges 12.3 and 12.4, respectively, and valve body rims, and are then extended further upward in the outflow direction and/or downward in the inflow direction, respectively. As in the embodiment of FIGS. 5 and 6, the inner diameters of interior flange surfaces 30.9" and 30.10" are increased to compensate for the increased diameter of the valve body flanges 12.3, 12.4 to maintain the continuous gap 20 between all exterior surfaces of the split ring 30" and the corresponding opposed valve body exterior surfaces to accommodate the suturing fabric body 14.1 therebetween. The gap 20 is also maintained between the extended outflow and inflow band flanges 30.7", 30.8" and the opposed valve flange surfaces 12.5, 12.6 through self centering of the suturing ring 30" within the valve body flat-bottomed groove. Again, the gap 20 width need not be the same in all areas from the inflow side to the outflow side. This embodiment also discourages suturing directly through the extended outflow and inflow rim bands 14.4" and 14.5" in the toroidal shape valve configuration.

A tubular shaped blood flow channel is created by extending the suturing ring 30" in the inflow and/or outflow directions. The extended outflow and inflow rim bands 14.4" and 14.5" places the suturing ring fabric to metal valve base interface in the high velocity blood flow channel and discourages the formation of pannus. Because of the higher velocity of blood flow at this interface, neointimal overgrowth past the interface is discouraged and minimized. Only an extremely thin neointimal layer grows over the extended outflow and inflow rim bands 14.4" and 14.5". The length of extension in each direction may be on the order of 25%–75% of the width of the valve base 12, for example. The relationship of flat-bottomed groove(s) and flanges providing the tracking surface and rotational guide can be reversed as shown, for example, in FIGS. 9 and 10. In this case, the valve body 120 is formed with a circular major exterior wall 120.2 having a major valve body diameter. At least one annular flange 120.1 extends outward and around the exterior wall 120.2 having a flange diameter exceeding the valve body diameter and opposed surfaces 120.5 and 120.6 providing the rotational guide. The width and positioning of the annular flange 120.1 with respect to the major exterior wall 120.2 can be varied the depicted example.

Figure 9:
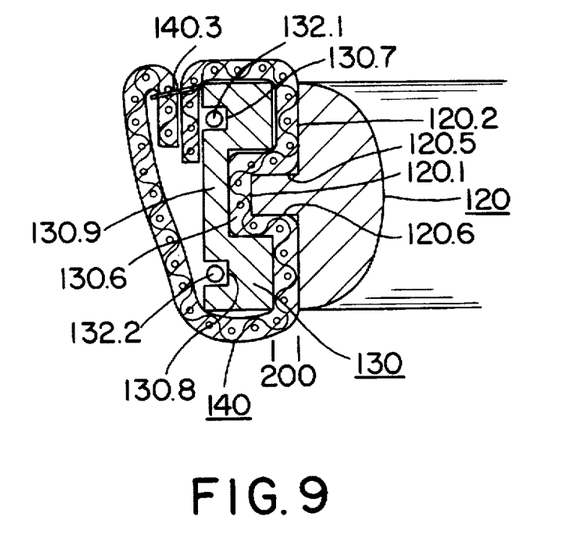
FIG. 9 is a cross-section view of a still further embodiment of the present invention, that may be implemented with the extended band flanges of the embodiments of FIGS. 5–8, wherein the relationship of flat-bottomed groove(s) and flanges is reversed.
Figure 10:
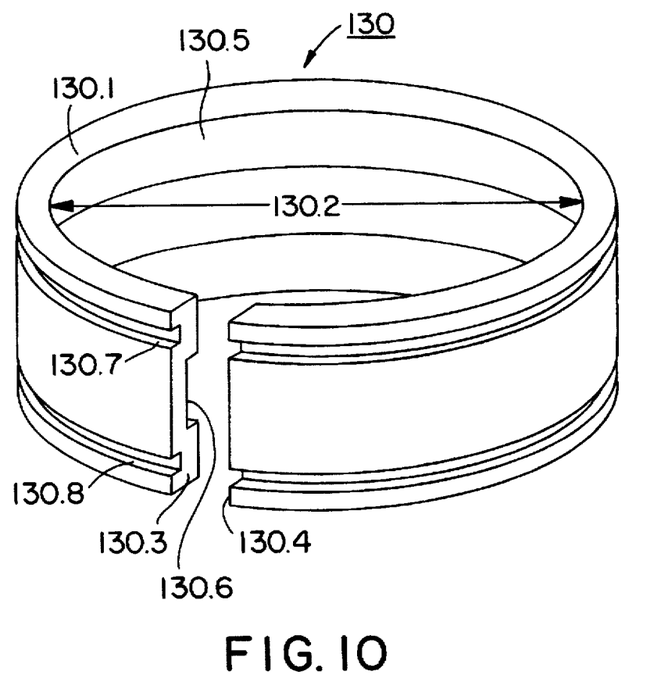
FIG. 10 is a perspective view of the split ring employed in the embodiment of FIG. 9.

The split ring 130 is again formed as a band 130.1 and has opposed split ring ends 130.3 and 130.4 and an interior wall 130.5 having a major band diameter 130.2 when the split ends 130.3 and 130.4 are maintained in abutting contact. The major band diameter 130.2 exceeds the major valve body diameter to accommodate the annular section of the suturing ring fabric 140 in the continuous gap 200.

The interior wall 130.5 is formed with a flat-bottomed groove 130.6 having a groove diameter and width exceeding the major diameter and width of the annular flange 120.1 to provide the tracking surface and continuous gap 200. The rotational torque is again established by the area of compression of the annular section of the suturing ring fabric 140 within the continuous gap 200 as described above. The cushioning effect of the compressed suturing fabric layer again self centers the suturing ring 140 and band 130.1 with respect to the annular flange 120.1. The width tolerances of gap 200 may vary along its path to ease manufacture of the opposed surfaces while a narrow overall rotational torque range may be specified and readily attained.

The steps of assembling the suturing ring 140 to the valve body 120 are completed as described above. However, the opposed split ends 130.3 and 130.4 are held together by a contact maintaining mechanism on either side of the flat-bottomed groove 130.6 and annular flange 120.1. In this case, upper and lower retaining grooves 130.7 and 130.8 are formed in the exterior wall 130.9 of band 130.1 that receive cords 132.1 and 132.2, respectively, or the like. The cords 132.1 and 132.2 are tightened within the upper and lower retaining grooves, and the suturing ring fabric edges are sewn together at seam 140.3 to complete the assembly.

The split ring 130 may be formed with the inflow and outflow extensions of the type shown in the embodiments of FIGS. 5–8 and for the reasons described above. The suturing ring fabric 140 may be shaped to form a flange in the manner of the flange depicted in FIG. 7.

During the implantation of the embodiments of the heart valve depicted in FIGS. 3–10, a convenient holder attached to the valve body 12, 12' is employed to properly position the suturing ring 14, 14' in a heart tissue orifice which has been prepared to receive the prosthetic valve. The suturing ring 14, 14' is sutured by the surgeon to the heart tissue around the heart tissue orifice in the accepted manner for aortic and mitral heart valves. The valve body 12, 12' may then be rotated within the suturing ring 14, 14' as desired by the surgeon so that the valve mechanism may operate without interference from the surrounding tissue. During manual rotation, a counter rotation force is gently applied by the surgeon to the suturing ring 14, 14' to further reduce stresses on the sutured heart tissue. As mentioned above, the torque required for rotation of the valve body should be sufficiently small as to avoid rotational forces tending to loosen the sutures or damage the heart tissue which has been sutured to the suturing ring but yet should be sufficiently high as to prevent the valve body from rotating within the suturing ring when heart function has been restored.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. An implantable heart valve having at least one valve mechanism movable between an open position and a closed position, a valve body for supporting the valve mechanism having a circular exterior wall extending between inflow and outflow valve body rims and an interior valve opening annulus, and an exterior rotatable suturing ring formed of suturing ring fabric for suturing the heart valve to a natural heart tissue orifice, apparatus for securing the suturing ring for rotation about the valve body exterior wall upon application of a rotational torque comprising:

rotational guide means formed on the annular exterior wall of the heart valve body providing a rotational guide about which the suturing ring is rotatable; and means formed within the suturing ring for compressing an annular section of the suturing ring fabric into engagement against the rotational guide with a consistent force, the compressing means further comprising:

a split ring formed of ring-shaped band having opposed split ring ends, an interior wall having a major diameter and a tracking surface shaped to be engaged by and spaced apart from the rotational guide and to provide a continuous gap when the split ring ends are maintained in contact for receiving the annular section of the sewing ring fabric therebetween, the ring shaped band being formed of a resilient material and adapted to be expanded in diameter to separate the split ring ends and to allow the split ring band tracking surface to be aligned with the rotational guide; and contact maintaining means for maintaining the split ring ends in contact such that a continuous gap is maintained between the rotational guide and the tracking surface, whereby the suturing ring fabric is entrapped in the continuous gap and frictionally engages the opposed tracking surface and rotational guide providing a consistent frictional force that may be overcome by a consistent rotational torque applied between the valve body and the suturing ring for rotation thereof.

2. The heart valve of claim 1 wherein the split ring within the suturing ring fabric further comprises extended inflow and outflow band flanges extending at least to the inflow and outflow valve body rims.

3. The heart valve of claim 1 wherein the split ring within the suturing ring fabric further comprises an extended inflow band flange extending at least to the inflow valve body rim.

4. The heart valve of claim 1 wherein the split ring within the suturing ring fabric further comprises an extended outflow band flange extending at least to the outflow valve body rim.

5. The heart valve of claim 1 wherein:

the rotational guide means comprises an annular valve body flange extending outward of the exterior wall of the valve body; and the tracking surface is an annular groove formed in the interior wall of the ring-shaped band adapted to fit over the annular valve body flange providing a gap therebetween for entrapping an annular section of the suturing ring fabric in the gap.

6. The heart valve of claim 1 wherein:

the rotational guide means comprises an annular exterior wall having a flat-bottomed groove formed therein between outflow and inflow groove flanges having flange diameters exceeding the flat-bottomed groove diameter for defining a gap from the interior wall of the ring-shaped band disposed circumferentially within the groove for receiving an annular section of suturing ring fabric.

7. The heart valve of claim 1 wherein the suturing ring fabric further comprises a biocompatible fabric of a mesh weave having interstices permeable to tissue ingrowth and fashioned into a generally toroidal shaped fabric ring having an interior directed surface adapted to be fitted against the valve body rotational guide means and an exterior directed surface adapted to receive sutures for implantation of the valve in a prepared site in the heart and defining an outflow annular rim fabric surface adjacent the outflow rim of the valve body and an inflow annular rim fabric surface adjacent the inflow rim of the valve body.

8. The heart valve of claim 7 wherein the split ring within the suturing ring fabric further comprises extended inflow and outflow band flanges extending past the inflow and outflow valve body rims thereby extending the inflow and outflow annular rim fabric surfaces into high blood velocity regions.

9. The heart valve of claim 7 wherein the split ring within the suturing ring fabric further comprises an extended inflow band flange extending past the inflow valve body rim thereby extending the inflow annular rim fabric surface into a high inflow blood velocity region.

10. The heart valve of claim 7 wherein the split ring within the suturing ring fabric further comprises an extended outflow band flange extending past the outflow valve body rim thereby extending the outflow annular rim fabric surface into a high outflow blood velocity region.

11. The heart valve of claim 7 wherein the split ring within the suturing ring fabric further comprises extended inflow and outflow band flanges extending at least to the inflow and outflow valve body rims thereby separating the exterior directed surface of the suturing ring fabric from the inflow and outflow annular rim fabric surfaces and inhibiting the extension of suturing knots and tails into the valve body annulus.

12. The heart valve of claim 11 wherein the split ring within the suturing ring fabric further comprises extended inflow and outflow band flanges extending past the inflow and outflow valve body rims.

13. The heart valve of claim 7 wherein the split ring within the suturing ring fabric further comprises an extended inflow band flange extending past the inflow valve body rim, thereby separating the exterior directed surface of the suturing ring fabric from the inflow annular rim fabric surface and inhibiting the extension of suturing knots and tails into the valve body annulus.

14. The heart valve of claim 13 wherein the split ring within the suturing ring fabric further comprises an extended inflow band flange extending past the inflow valve body rim.

15. The heart valve of claim 7 wherein the split ring within the suturing ring fabric further comprises an extended outflow band flange extending past the outflow valve body rim, thereby separating the exterior directed surface of the suturing ring fabric from the outflow annular rim fabric surface and inhibiting the extension of suturing knots and tails into the valve body annulus.

16. The heart valve of claim 15 wherein the split ring within the suturing ring fabric further comprises an extended outflow band flange extending past the outflow valve body rim.

17. An implantable heart valve having at least one valve mechanism movable between an open position and a closed position, a valve body for supporting the valve mechanism, and an exterior rotatable suturing ring for suturing to a natural heart tissue orifice and allowing rotation of the valve body with respect to the suturing ring, the valve body having an annular exterior wall having a groove formed therein between outflow and inflow flanges having flange diameters exceeding a diameter of the groove for receiving the suturing ring disposed circumferentially around the groove, the suturing ring further comprising:

a biocompatible fabric of a mesh weave having interstices permeable to tissue ingrowth and first and second axial ends fastened into a generally toroidal shaped fabric ring having an interior directed surface adapted to be fitted against the valve body groove and an outward directed surface adapted to receive sutures for implantation of the valve in a prepared site in the heart; and means disposed entirely within interior of the fabric ring for fitting the interior directed surface of the fabric ring against the valve body groove leaving the outward directed surface exposed and defining an outflow annular rim surface adjacent the outflow flange of the valve body and an inflow annular rim surface adjacent the inflow flange of the valve body, the fitting means further comprising:

a split ring formed of ring-shaped band having opposed split ring ends adapted to be separated apart to allow the split ring to be fitted within the valve body groove and abutted together to form a continuous circular band having a fixed inner diameter greater than the groove diameter and less than the inflow and outflow flange diameters; and contact maintaining means for maintaining the split ring ends in abutting contact such that a fixed gap is maintained between the split ring and the valve body groove, whereby the interior directed surface of the suturing ring fabric is entrapped in the fixed gap and frictionally engages the split ring and valve body groove providing a constant frictional force that may be overcome by rotational torque applied between the valve body and the suturing ring for rotation thereof.

18. The heart valve of claim 17 wherein the split ring further comprises inflow and outflow band flanges extending at least over the inflow and outflow valve body flanges within the fabric ring to provide a barrier to penetration of suture needles through the inflow and outflow annular rim surfaces.

19. The heart valve of claim 17 wherein the split ring further comprises an inflow band flange extending at least over the inflow valve body flange within the fabric ring to provide a barrier to penetration of suture needles through the inflow annular rim surface.

20. The heart valve of claim 17 wherein the split ring further comprises an outflow band flange extending over the at least the outflow valve body flange within the fabric ring to provide a barrier to penetration of suture needles through the outflow annular rim surface.

21. The heart valve of claim 17 wherein the split ring further comprises inflow and outflow band flanges extending over the inflow and outflow valve body flanges within the fabric ring, respectively, a distance effecting an increase in blood flow velocity past the inflow and outflow annular rims to inhibit formation of pannus and pannus overgrowth over the interface between the inflow and outflow valve body flanges and the adjacent inflow and outflow annular rims, respectively.

22. The heart valve of claim 17 wherein the split ring further comprises an inflow band flange extending over the inflow valve body flange within the fabric ring a distance effecting an increase in blood flow velocity past the inflow annular rim to inhibit formation of pannus and pannus overgrowth over the interface between the inflow valve body flange and the adjacent inflow annular rim.

23. The heart valve of claim 17 wherein the split ring further comprises an outflow band flange extending over the outflow valve body flange within the fabric ring a distance effecting an increase in blood flow velocity past the outflow annular rim to inhibit formation of pannus and pannus overgrowth over the interface between the outflow valve body flange and the adjacent outflow annular rim.

24. An implantable heart valve having at least one valve mechanism movable between an open position and a closed position, a valve body for supporting the valve mechanism having an exterior wall extending between inflow and outflow valve rims and an interior valve opening annulus, and an exterior rotatable suturing ring formed of suturing ring fabric for suturing the heart valve to a natural heart tissue orifice, apparatus for securing the suturing ring for rotation about the valve body exterior wall upon application of a rotational torque comprising:

rotational guide means formed on the annular exterior wall of the heart valve body providing a rotational guide about which the suturing ring is rotatable;

split ring means formed within the suturing ring for supporting said suturing ring in a generally toroidal shaped fabric ring, said fabric having an annular section adapted to be fitted against the valve body rotational guide means and an outward directed surface adapted to receive sutures for implantation of the valve in a prepared site in the heart and defining an outflow annular rim fabric surface adjacent the outflow rim of the valve body and an inflow annular rim fabric surface adjacent the inflow rim of the valve body, said split ring means compressing said annular section of the suturing ring fabric into engagement against the rotational guide with a consistent force; and means for maintaining said split ring means with a constant diameter.

25. The heart valve of claim 24 wherein the split ring within the suturing ring fabric further comprises extended inflow and outflow band flanges extending past the inflow and outflow valve body rims thereby extending the inflow and outflow annular rim fabric surfaces into high blood velocity regions.

26. The heart valve of claim 24 wherein the split ring within the suturing ring fabric further comprises an extended inflow band flange extending past the inflow valve body rim thereby extending the inflow annular rim fabric surface into a high inflow blood velocity region.

27. The heart valve of claim 24 wherein the split ring within the suturing ring fabric further comprises an extended outflow band flange extending past the outflow valve body rim thereby extending the outflow annular rim fabric surface into a high outflow blood velocity region.

28. The heart valve of claim 24 wherein the split ring within the suturing ring fabric further comprises extended inflow and outflow band flanges extending at least to the inflow and outflow valve body rims thereby separating the exterior directed surface of the suturing ring fabric from the inflow and outflow annular rim fabric surfaces and inhibiting the extension of suturing knots and tails into the valve body annulus.

29. The heart valve of claim 28 wherein the split ring within the suturing ring fabric further comprises extended inflow and outflow band flanges extending past the inflow and outflow valve body rims.

30. The heart valve of claim 24 wherein the split ring within the suturing ring fabric further comprises an extended inflow band flange extending past the inflow valve body rim, thereby separating the exterior directed surface of the suturing ring fabric from the inflow annular rim fabric surface and inhibiting the extension of suturing knots and tails into the valve body annulus.

31. The heart valve of claim 30 wherein the split ring within the suturing ring fabric further comprises an extended inflow band flange extending past the inflow valve body rim.

32. The heart valve of claim 24 wherein the split ring within the suturing ring fabric further comprises an extended outflow band flange extending past the outflow valve body rim thereby separating the exterior directed surface of the suturing ring fabric from the outflow annular rim fabric surface and inhibiting the extension of suturing knots and tails into the valve body annulus.

33. The heart valve of claim 32 wherein the split ring within the suturing ring fabric further comprises an extended outflow band flange extending past the outflow valve body rim.

* * * * *

UNITED STATES PATENT AND TRADEMARK OFFICE
CERTIFICATE OF CORRECTION

PATENT NO. : 5,766,240
DATED : June 16, 1998
INVENTOR(S) : Johnson

It is certified that error appears in the above-identified patent and that said Letters Patent is hereby corrected as shown below:

Col. 14, Line 62: "said fabric having an" should be "said fabric ring having an"

Signed and Sealed this

Fourth Day of May, 1999

*Attest:*

Q. TODD DICKINSON

*Attesting Officer*     *Acting Commissioner of Patents and Trademarks*